United States Patent
Hsieh et al.

(10) Patent No.: US 8,942,341 B2
(45) Date of Patent: Jan. 27, 2015

(54) METHOD OF DOSE REDUCTION FOR CT IMAGING AND APPARATUS FOR IMPLEMENTING SAME

(75) Inventors: Jiang Hsieh, Brookfield, WI (US);
Abdelaziz Ikhlef, Hartland, WI (US);
Paavana Sainath, Oconomowoc, WI (US); Xiaoye Wu, Rexford, NY (US);
Roman Melnyk, Pewaukee, WI (US)

(73) Assignee: General Electric Company, Schenectady, NY (US)

( * ) Notice: Subject to any disclaimer, the term of this patent is extended or adjusted under 35 U.S.C. 154(b) by 818 days.

(21) Appl. No.: 13/223,665

(22) Filed: Sep. 1, 2011

(65) Prior Publication Data

US 2013/0058451 A1    Mar. 7, 2013

(51) Int. Cl.
| A61B 6/03 | (2006.01) |
| G21K 3/00 | (2006.01) |
| A61B 6/06 | (2006.01) |
| A61B 6/00 | (2006.01) |

(52) U.S. Cl.
CPC . *A61B 6/032* (2013.01); *A61B 6/06* (2013.01); *A61B 6/542* (2013.01); *A61B 6/4078* (2013.01); *A61B 6/503* (2013.01)
USPC ............................................. 378/16; 378/158

(58) Field of Classification Search
USPC ............................ 378/4, 19, 16, 156, 157.158
See application file for complete search history.

(56) References Cited

U.S. PATENT DOCUMENTS

| 6,259,098 | B1 | 7/2001 | Vafi et al. | |
| 6,280,084 | B1 * | 8/2001 | Toth | 378/207 |
| 6,389,096 | B1 | 5/2002 | Hoffman et al. | |
| 6,740,883 | B1 | 5/2004 | Stodilka et al. | |
| 7,016,455 | B2 | 3/2006 | Bruder et al. | |
| 7,082,189 | B2 * | 7/2006 | Yahata et al. | 378/156 |
| 7,088,799 | B2 * | 8/2006 | Hoffman | 378/5 |
| 7,127,096 | B2 | 10/2006 | Kaufman et al. | |
| 7,149,331 | B1 | 12/2006 | Kaufman et al. | |
| 7,254,216 | B2 * | 8/2007 | Thandiackal et al. | 378/159 |
| 7,409,035 | B2 | 8/2008 | Kaufman et al. | |
| 7,522,744 | B2 | 4/2009 | Bai et al. | |
| 7,564,940 | B2 | 7/2009 | Mattson et al. | |
| 7,746,974 | B2 | 6/2010 | Shukla | |
| 7,782,999 | B2 | 8/2010 | Lewalter et al. | |
| 7,787,112 | B2 | 8/2010 | Rahn et al. | |
| 7,888,647 | B2 | 2/2011 | Warner et al. | |
| 7,894,576 | B2 | 2/2011 | Carmi | |
| 7,933,010 | B2 | 4/2011 | Rahn et al. | |
| 2001/0033030 | A1 * | 10/2001 | Leedy | 257/777 |

\* cited by examiner

*Primary Examiner* — Irakli Kiknadze
(74) *Attorney, Agent, or Firm* — Ziolkowski Patent Solutions Group, SC (57) ABSTRACT

A CT system includes an x-ray source configured to project an x-ray beam toward an object, a detector array, and a bowtie filter. The bowtie filter includes a first x-ray filtration region positioned to attenuate x-rays that pass through an isochannel of the detector array, a second x-ray filtration region positioned to attenuate x-rays that pass through channels of the detector array that are offcenter in a channel direction from the isochannel, and an x-ray attenuation material positionable to attenuate the x-rays that pass through the channels of the detector array that are offcenter in the channel direction from the isochannel. The CT system also includes a data acquisition system (DAS) connected to the detector array and configured to receive outputs from the detector array, and a computer programmed to acquire projections of imaging data of the object, and generate an image of the object using the imaging data.

24 Claims, 9 Drawing Sheets

METHOD OF DOSE REDUCTION FOR CT IMAGING AND APPARATUS FOR IMPLEMENTING SAME

BACKGROUND OF THE INVENTION

Embodiments of the invention relate generally to diagnostic imaging and, more particularly, to a method and apparatus of dose reduction in an imaging application.

Typically, in computed tomography (CT) imaging systems, an x-ray source emits a fan-shaped beam toward a subject or object, such as a patient or a piece of luggage. Hereinafter, the terms "subject" and "object" shall include anything capable of being imaged. The beam, after being attenuated by the subject, impinges upon an array of radiation detectors. The intensity of the attenuated beam radiation received at the detector array is typically dependent upon the attenuation of the x-ray beam by the subject. Each detector element of the detector array produces a separate electrical signal indicative of the attenuated beam received by each detector element. The electrical signals are transmitted to a data processing system for analysis which ultimately produces an image.

Generally, the x-ray source and the detector array are rotated about the gantry within an imaging plane and around the subject. X-ray sources typically include x-ray tubes, which emit the x-ray beam at a focal point. X-ray detectors typically include a collimator for collimating x-ray beams received at the detector, a scintillator for converting x-rays to light energy adjacent the collimator, and photodiodes for receiving the light energy from the adjacent scintillator and producing electrical signals therefrom.

Typically, each scintillator of a scintillator array converts x-rays to light energy. Each scintillator discharges light energy to a photodiode adjacent thereto. Each photodiode detects the light energy and generates a corresponding electrical signal. The outputs of the photodiodes are then transmitted to the data processing system for image reconstruction.

With recent advances in CT clinical applications, it is desirable to cover an entire organ in a single gantry rotation and in a single projection, so that an entire cardiac acquisition can be completed in a single cardiac cycle. A heart can typically be covered in a cylindrical shaped region with a diameter of 25 cm (in an x-y plane) and a length of 12 cm (in a slice or z-direction) for most patients. In neural perfusion studies it is desirable to cover at least 12 cm along the patient long axis (in z-direction) while continuously scanning the patient during contrast uptake and washout. There are CT scanners on the market that cover, for example, 16 cm along the z-axis and 50 cm field-of-view (FOV) across the patient (in an x-y plane), which are well in excess of that necessary to provide imaging information for cardiac and neural perfusion studies. Thus, for cardiac and neural perfusion studies the region-of-interest (ROI) in the x-y plane is significantly smaller than the full detector coverage of 50 cm.

However, scanning a patient with a 50 cm FOV not only provides little additional relevant information but also results in additional dose to the patient. The cost of such a scanner can be prohibitive, as well. From a design point of view, it is desirable to reduce the coverage to a FOV (in x-y plane) that is slightly larger than the object-of-interests. For CT reconstruction, however, information outside the region-of-interest is necessary to faithfully reconstruct an object-of-interest. Without this information, typical truncation artifacts may result. Although recent attempts have been made to reconstruct images based on truncated projections, these reconstruction techniques typically result in unstable solutions or require specific knowledge inside the reconstruction FOV.

Therefore, it would be desirable to design an apparatus and method dose reduction in CT imaging while reducing overall cost of a CT system.

BRIEF DESCRIPTION OF THE INVENTION

The invention is a directed method and apparatus for dose reduction.

According to one aspect, a CT system includes a rotatable gantry having an opening to receive an object to be scanned, an x-ray source configured to project an x-ray beam toward the object, a detector array having a width in a slice-direction and configured to detect x-rays passing through the object, and a first bowtie filter positioned between the x-ray source and the opening. The first bowtie filter includes a first x-ray filtration region positioned to attenuate x-rays that pass through an isochannel of the detector array, a second x-ray filtration region positioned to attenuate x-rays that pass through channels of the detector array that are offcenter in a channel direction from the isochannel, and an x-ray attenuation material positionable to attenuate the x-rays that pass through the channels of the detector array that are offcenter in the channel direction from the isochannel. The CT system also includes a data acquisition system (DAS) connected to the detector array and configured to receive outputs from the detector array, and a computer programmed to acquire projections of imaging data of the object from the DAS, and generate an image of the object using the imaging data.

According to another aspect, a method of CT imaging includes projecting a beam of x-rays through a central portion of a bowtie filter and to a central portion of a detector array that includes an isochannel of the detector array, and projecting the beam of x-rays through a first non-central portion of the bowtie filter, the first non-central portion of the bowtie filter offset in a channel direction from the central portion of the bowtie filter, to a first non-central portion of the detector array, wherein the first non-central portion of the bowtie filter has a first x-ray attenuating material attached thereto.

According to yet another aspect, a non-transitory computer readable storage medium having stored thereon a computer program comprising instruction which, when executed by a computer, cause the computer to obtain x-ray imaging data that is generated in a detector from x-rays that pass through a central region of a first portion of a bowtie filter that defines a first region-of-interest (ROI) and includes an isochannel of the detector, obtain x-ray imaging data that is generated in the detector from x-rays that pass through two regions of the first portion of the bowtie filter, wherein the two regions are offset in opposite channel directions from the isochannel, and wherein the x-ray imaging data from the two regions of the bowtie filter is generated from x-rays that pass through an x-ray attenuation material that is a material different from a material of the bowtie filter, and generate an image using the x-ray imaging data.

Various other features and advantages will be made apparent from the following detailed description and the drawings.

BRIEF DESCRIPTION OF THE DRAWINGS

The drawings illustrate preferred embodiments presently contemplated for carrying out the invention.

In the drawings.

DETAILED DESCRIPTION OF THE PREFERRED EMBODIMENT

The operating environment of the invention is described with respect to a sixty-four-slice computed tomography (CT) system. However, it will be appreciated by those skilled in the art that the invention is equally applicable for use with other multi-slice configurations. Moreover, the invention will be described with respect to the detection and conversion of x-rays. However, one skilled in the art will further appreciate that the invention is equally applicable for the detection and conversion of other high frequency electromagnetic energy. The invention will be described with respect to a "third generation" CT scanner, but is equally applicable with other CT systems.

Figure 1:
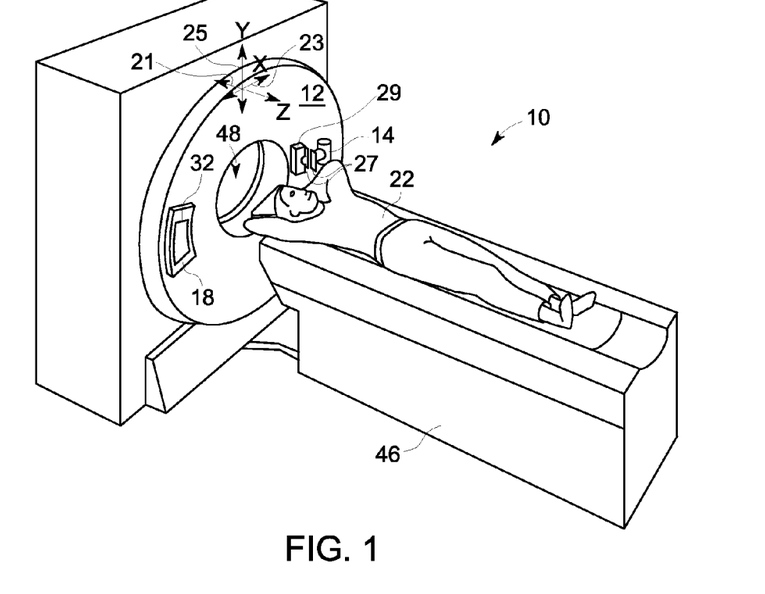
FIG. 1 is a pictorial view of a CT imaging system.
Figure 2:
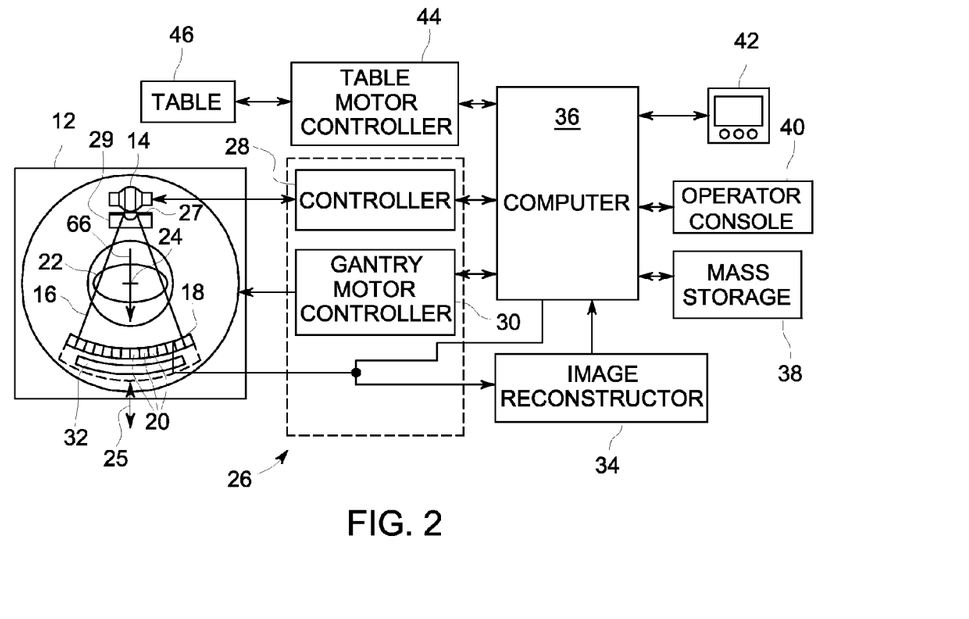
FIG. 2 is a block schematic diagram of the system illustrated in FIG. 1.

Referring to FIGS. 1 and 2, a computed tomography (CT) imaging system 10 is shown as including a gantry 12 representative of a "third generation" CT scanner. Gantry 12 has an x-ray source 14 that projects a beam of x-rays 16 toward a detector assembly 18 on the opposite side of the gantry 12. Imaging system 10 includes a pre-patient collimator 27 and a bowtie filter 29. Detector assembly 18 is formed by a plurality of detectors 20 and data acquisition systems (DAS) 32. The plurality of detectors 20 sense the projected x-rays 16 that pass through medical patient 22. DAS 32 converts the data from detectors 20 to digital signals for subsequent processing. Each detector 20 produces an analog electrical signal that represents the intensity of an impinging x-ray beam and hence the attenuated beam as it passes through the patient 22. During a scan to acquire x-ray projection data, gantry 12 and the components mounted thereon rotate about a center of rotation 24.

Rotation of gantry 12 and the operation of x-ray source 14 are governed by a control mechanism 26 of CT system 10. Control mechanism 26 includes a controller 28 that provides power and timing signals to an x-ray source 14 as well as motion control for operation of pre-patient collimator 27 and bowtie filter 29, and control mechanism 26 includes a gantry motor controller 30 that controls the rotational speed and position of gantry 12. An image reconstructor 34 receives sampled and digitized x-ray data from DAS 32 and performs high speed reconstruction. The reconstructed image is applied as an input to a computer 36 which stores the image in a mass storage device 38.

Computer 36 also receives commands and scanning parameters from an operator via console 40 that has some form of operator interface, such as a keyboard, mouse, voice activated controller, or any other suitable input apparatus. An associated display 42 allows the operator to observe the reconstructed image and other data from computer 36. The operator supplied commands and parameters are used by computer 36 to provide control signals and information to DAS 32, x-ray controller 28 and gantry motor controller 30. In addition, computer 36 operates a table motor controller 44 which controls a motorized table 46 to position patient 22 and gantry 12. Particularly, table 46 moves patients 22 through a gantry opening 48 of FIG. 1 in whole or in part.

As commonly understood in the art, patient 22 is generally translated along a z-direction 21, commonly referred to as a slice-direction, of gantry 12. As also commonly understood in the art, detector assembly 18 is caused to rotate circumferentially in an x-direction 23, or channel direction, of gantry 12. Thus, x-rays 16 travel generally in a y-direction 25 and through detector assembly 18 as they emit from x-ray source 14 and pass through patient 22.

Figure 3:
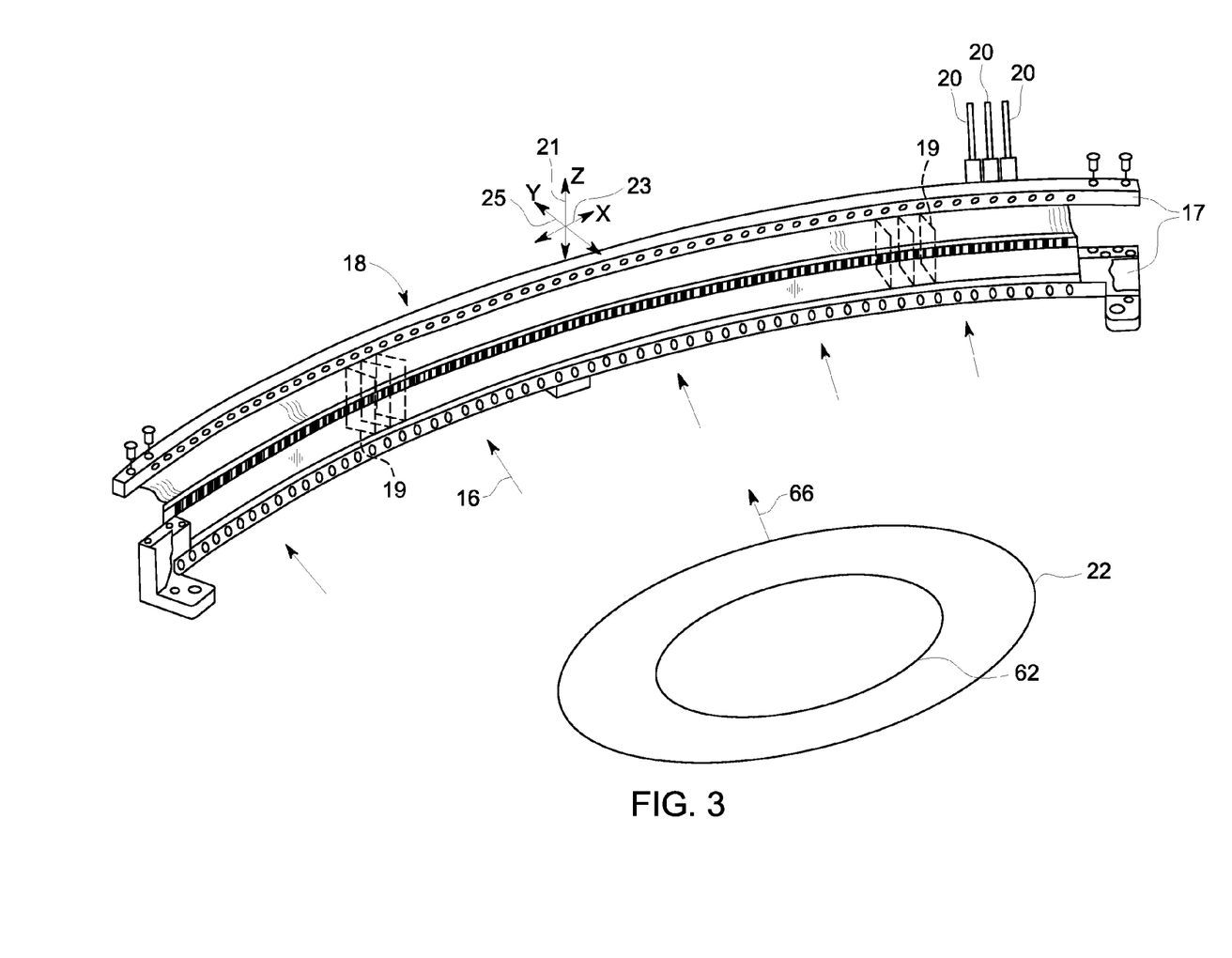
FIG. 3 is a perspective view of one embodiment of a CT system detector array.

As shown in FIG. 3, detector assembly 18 includes rails 17. Commonly, detector assembly 18 may include collimating blades or plates 19 placed therebetween. Plates 19 are positioned to collimate x-rays 16 before such beams impinge upon, for instance, detector 20 of FIG. 4 positioned on detector assembly 18. In one embodiment, detector assembly 18 includes 57 detectors 20, each detector 20 having an array size of 64×16 of pixel elements 50. As a result, detector assembly 18 has 64 rows and 912 columns (16×57 detectors) which allows 64 simultaneous slices of data to be collected with each rotation of gantry 12. Thus, consistent with FIGS. 1 and 2, z-direction 21 (or slice direction), x-direction 23 (or channel direction), and y-direction 25 are illustrated.

Figure 4:
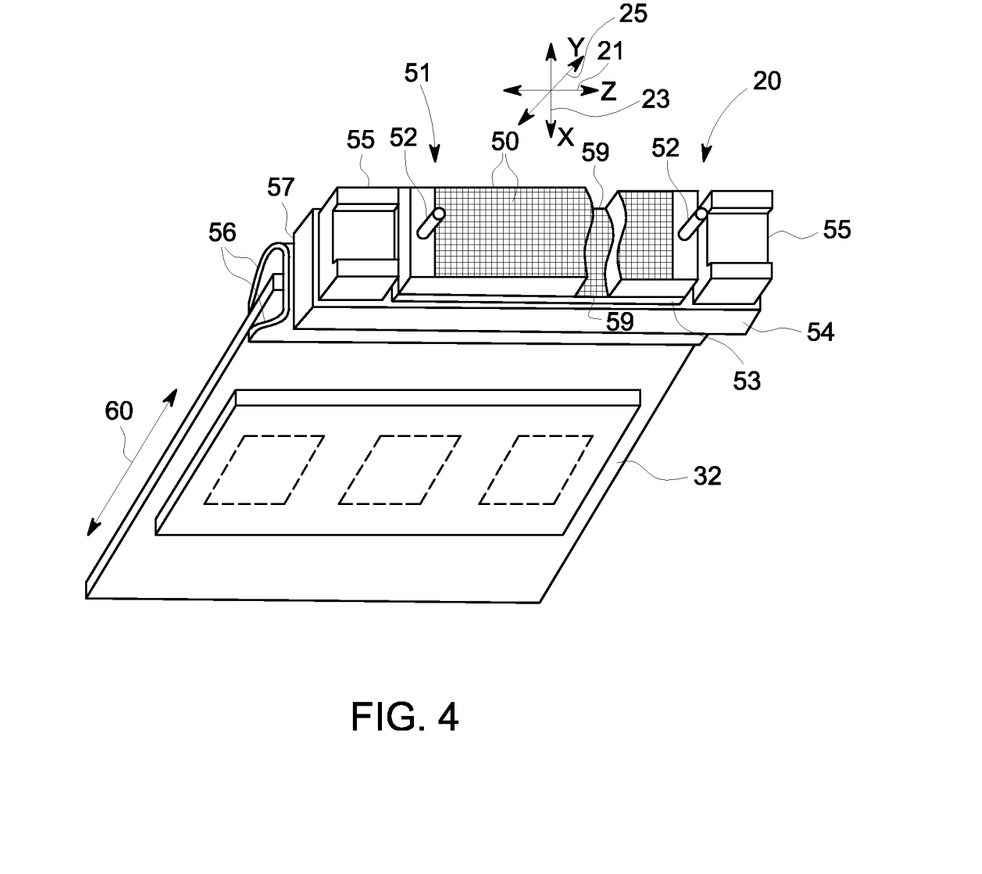
FIG. 4 is a perspective view of one embodiment of a detector.

Referring to FIG. 4, detector 20 includes DAS 32, with each detector 20 including a number of detector elements 50 arranged in pack 51. Detectors 20 include pins 52 positioned within pack 51 relative to detector elements 50. Pack 51 is positioned on a backlit diode array 53 having a plurality of diodes 59. Backlit diode array 53 is in turn positioned on multi-layer substrate 54. Spacers 55 are positioned on multi-layer substrate 54. Detector elements 50 are optically coupled to backlit diode array 53, and backlit diode array 53 is in turn electrically coupled to multi-layer substrate 54. Flex circuits 56 are attached to face 57 of multi-layer substrate 54 and to DAS 32. Detectors 20 are positioned within detector assembly 18 by use of pins 52.

In the operation of one embodiment, x-rays impinging within detector elements 50 generate photons which traverse pack 51, thereby generating an analog signal which is detected on a diode within backlit diode array 53. The analog signal generated is carried through multi-layer substrate 54, through flex circuits 56, to DAS 32 wherein the analog signal is converted to a digital signal. Consistent with the earlier discussion, z-direction 21 defines also a slice direction and, as understood in the art, the number of detector elements 50 positioned along z-direction 21 and in detector 20 defines the number of imaging slices obtainable in an imaging system, such as imaging system 10 of FIGS. 1 and 2. Typically, the number of slices or detector elements 50 along z-direction 21 may be 16, 64, or 256. However, it is contemplated that the invention is not to be so limited, and that any number of slices may be collimated, according to the invention. X-direction 23, or channel direction, is also illustrated as it relates to detector 20. Typically, as stated, each detector 20 includes 16 detector elements 50 in x-direction 23, and there are typically 57 such detectors 20 positioned in detector assembly 18. However, it is contemplated that the invention is not to be so limited, and that any number of channels may be collimated, according to the invention. Y-direction 25 is illustrated, having a direction 60 that is generally parallel with DAS 32.

Referring back to FIG. 3, three exemplary detectors 20 (also referred to as detector modules) are illustrated therein (of the 57 modules described above, for example). During imaging of, for instance, patient 22 of FIGS. 1 and 2, a region-of-interest (ROI) 62 may be imaged by obtaining imaging data from the detectors 20, mounted on detector assembly 18. Thus, as gantry 12 is rotated, x-rays 16 emit from source 14, through patient 22, and are received by detectors 20. Typically, imaging data is obtained of ROI 62 as either a helical or an axial scan is performed, as known in the art. Commonly, a centermost channel, at the center of detector assembly 18 along x-direction 23, is defined as the isochannel or isocenter, which receives x-rays that pass along a centermost ray 66 to detector assembly 18. For further illustration, referring back to FIG. 2, ray 66 shows centermost ray 66 passing generally through center-of-rotation 24.

Figure 5:
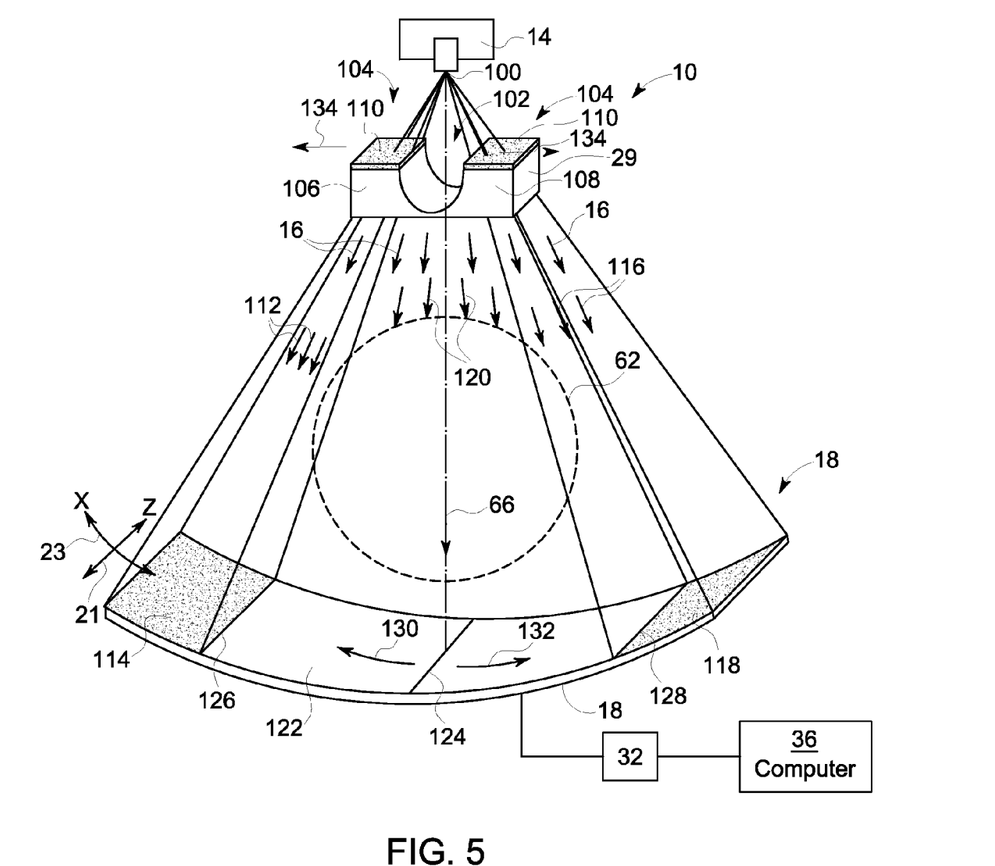
FIG. 5 illustrates a bowtie filter having x-ray filtration regions according to an embodiment of the invention.

According to the invention, filtration is added to a pre-patient collimator to minimize a signal outside the ROI. This can be accomplished by adding a few millimeters of attenuating thin plates, such as aluminum or copper, to outside channel regions of a bowtie filter, typically having an amount of attenuation per unit thickness that is greater than the bowtie filter itself. As known in the art, a typical bowtie may be fabricated using aluminum, plastic, and other materials for providing a controllable amount of attenuation using materials that are generally low cost for fabrication, machining, and use. According to one embodiment, 3 mm of copper is used outside the ROI. Thus, FIG. 5 illustrates a bowtie filter 29, detector array 18, x-ray source 14, and ROI 62, corresponding to system 10 and components illustrated in FIGS. 1-4, are illustrated in a perspective view. For simplicity of illustration, other components of system 10, such as gantry 12 for example, are not shown.

Referring to FIG. 5, system 10 includes a focal spot 100 of x-ray source 14, from which x-rays 16 emit toward detector array 18. Bowtie filter 29 includes a first x-ray filtration region 102 and a second x-ray filtration region 104 which itself includes a first sub-region 106 and a second sub-region 108. Sub-regions 106, 108 include an x-ray attenuation material 110 that is positioned to attenuate x-rays 16 that pass from focal spot 100, through sub-regions 106, 108 and to detector array 18. More specifically, x-rays 112 that pass through first sub-region 106 of bowtie filter 29 pass to a first sub-region 114 of detector array 18, and x-rays 116 that pass through second sub-region 108 of bowtie filter 29 pass to a second sub-region 118 of detector array 18. Conversely, x-rays 120 that pass through first x-ray filtration region 102 of bowtie filter 29 pass to a central detector region 122, which includes an isochannel 124 that is a channel positioned to receive x-rays 16 that pass along centermost ray 66. As described, detector array 18 is electrically coupled to DAS 32, which is coupled to computer 36. Thus, computer 36 is programmed to acquire projections of image data from DAS 32, which is configured to acquire image data from detector array 18.

Central detector region 122 and first sub-region 114 are separated by a first boundary 126, and central detector region 122 and second sub-region 118 are separated by a second boundary 128. Thus, first boundary 126 is located in a first channel direction 130 from isochannel 124, which is coincident with x-direction 23, and second boundary 128 is located in a second channel direction 132 from isochannel 124, likewise coincident with x-direction 23 but opposite first channel direction 130. First and second x-ray filtration regions 102, 104, along with corresponding first and second detector sub-regions 114, 118 and central detector region 122, are selected in order that ROI 62 is fully encompassed by first x-ray filtration region 102 and central detector region 122. One skilled in the art will recognize that ROI 62 may vary in size based on a patient to be imaged, thus x-ray filtration regions 102, 104 and corresponding detector sub-regions 114, 118 may be selected based on a range of sizes of ROI 62 that may be expected based on expected clinical use of system 10, for example.

Since a typical small bowtie filter may cover a 25 cm scan field-of-view (FOV), the addition of x-ray attenuation material 110 does not impact the functionality of a small bowtie filter, such as bowtie filter 29, when scanning objects. According to one embodiment, x-ray attenuation material 110 is a positionable material that is attached, either permanently or removeably (in order to swap out material 110) to first and second sub-regions 106, 108. Alternatively, according to another embodiment, x-ray attenuation material 110 can be added and removed dynamically when, for instance, cardiac scanning is required. That is, x-ray attenuation material 110 may be repositioned 134 dynamically and controlled by, for instance, controller 28 of system 10, such that x-rays 112 and 116 are attenuated by first and second sub-regions 106, 108 only of bowtie filter 29, and not by x-ray attenuation material 110, when desired.

Figure 6:
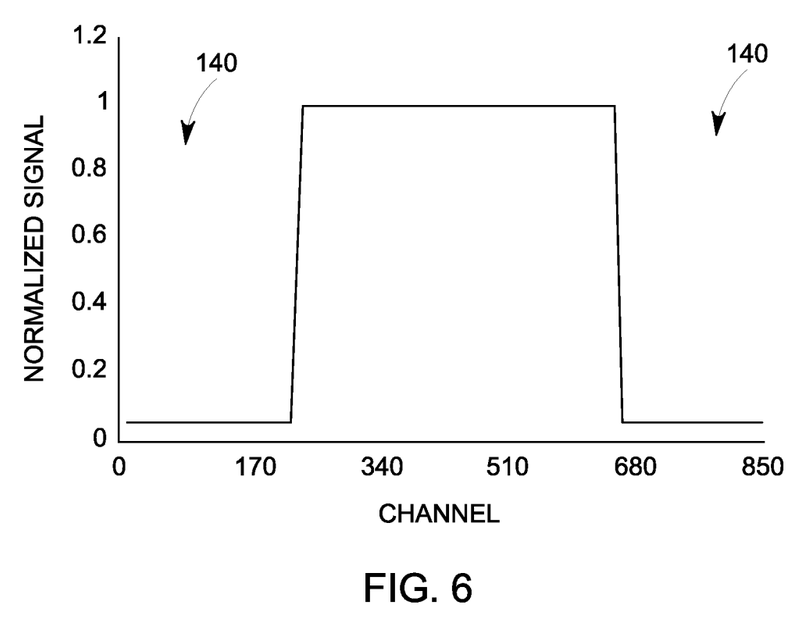
FIG. 6 shows an example of a relative x-ray intensity profile for a filtered x-ray beam.

In a preferred embodiment, the amount of filtration provided by x-ray attenuation material 110, when positioned in conjunction with first and second sub-regions 106, 108, reduces the x-ray flux in first and second sub-regions 114, 118 shown in FIG. 5 by a factor of 20 or more. That is, the radiation outside ROI 62 is essentially negligible as compared to the overall dose. FIG. 6 shows a relative intensity profile for an exemplary 3 mm thick filter. For a typical ROI 62 that is encompassed fully by central detector region 122, imaging data received at detector array 18 in first and second sub-regions 114, 118, outside of central detector region 122, may provide little additional information in the final images. However, an amount of x-ray energy outside of central detector region 122 at locations 140 may be useful or necessary in order to avoid truncation errors in the final images. Thus, it is desirable to receive approximate total energy received from x-rays 112, 116 received in first and second sub-regions 114, 118.

Figure 7:
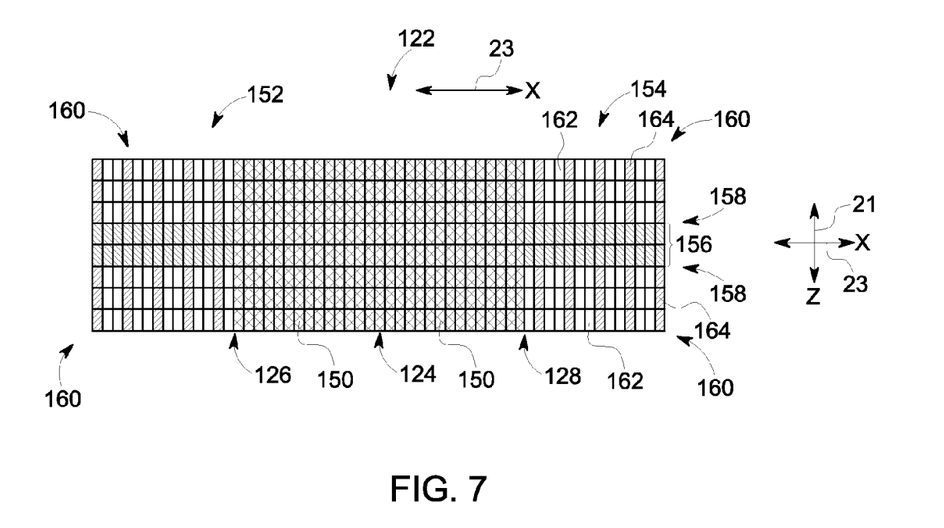
FIG. 7 illustrates an example of a depopulated x-ray detector according to an embodiment of the invention.

According to an embodiment of the invention, to reduce the cost of the detector some of the detector modules are removed outside the ROI as shown in FIG. 7. FIG. 7 depicts a depopulated plan view of detector array 18 that includes a configuration in which two out of three modules are removed. Central modules 150 correspond with central detector region 122 illustrated in FIG. 5, first sub-region 152 corresponds with first sub-region 114 of FIG. 5, and second sub-region 154 corresponds with second sub-region 118 of FIG. 5. According to this embodiment, center modules 156 are included as functioning modules in central detector region 122 as well as in detector sub-regions 152, 154. That is, along z-direction 21 and along the entire length along x-direction 23 of detector array 18, functional modules are included in order to provide a full FOV that extends beyond ROI 62. However, in the corners of detector array 18, module locations may be depopulated. Thus, defining z-boundaries 158, four corner regions 160 of modules are delineated between z-boundaries 158 and boundaries 126, 128.

As such, functional modules over a full FOV but in limited z coverage, between z-boundaries 158 for instance, provide the scanner with a way to collect full fidelity images in the entire FOV. Thus, in one mode of operation, pre-patient collimation in z-direction 21 is provided using, for instance, collimator 27 illustrated in FIGS. 1 and 2, which corresponds with a collimated width equals a width of center modules 156. In this mode, to obtain a full FOV, x-ray attenuation material 110 shown in FIG. 5 is either removed, or a large or medium bowtie is used where the thin plates are not present.

Referring to corner regions 160 of FIG. 5, empty blocks 162 represent the location of the removed modules, and blocks 164 represent functioning modules that are located therein. Note that since the role of such modules in blocks 164 is to provide generally sufficient information to avoid truncation artifacts, degraded modules can be used in these regions in four corner regions 160. Thus, when a more limited ROI scan is desired (to obtain imaging data of for instance ROI 62), the entire detector array 18 is exposed to x-rays 16, with the outer sub-regions 152, 154 filtered by thin plates or x-ray attenuation material 110 to minimize dose. Because there are gaps present in the detector in the outer region (i.e., in empty blocks 162), some of the x-ray photons that pass to detector array 18 are not detected. Because of the extremely low x-ray intensity in these regions, however, this lost information only represents a small fraction of dose efficiency. For the configuration shown in FIG. 7, for example, less than 1% of the x-ray flux is not detected. And, it is to be recognized that the degraded modules do not need be placed in a regular pattern. They can be scattered around the corner regions 160 and in blocks 164 to ensure sufficient information is collected for reconstruction.

Prior to the image reconstruction, the measured projections undergo additional processing to estimate missing information such as occurs because of empty blocks 162 where no detector modules are present. In one embodiment, two additional steps are added to estimate the missing information. The first step is to perform low-pass filtering on the measured signal outside the ROI. Note that the measured projections in these regions may contain higher noise due to the low x-ray intensity. For reconstruction purposes average signals may be used to estimate the profiles of the outer region to ensure accurate reconstruction in the ROI.

The next step is the estimate the missing signals due to the lack of detector modules in the gapped region. This can be performed by interpolating the measured signals (after smoothing operation described in the previous paragraph). The interpolation can be linear, spline, Lagrange, cubic Hermite, high-order Lagrange, and other methods. If desired, Fourier interpolation can be used to further preserve the frequency contents. After the missing projection samples are replaced by the interpolated samples, conventional reconstruction algorithms can be used to reconstruct the image in the region-of-interest.

Figure 8:
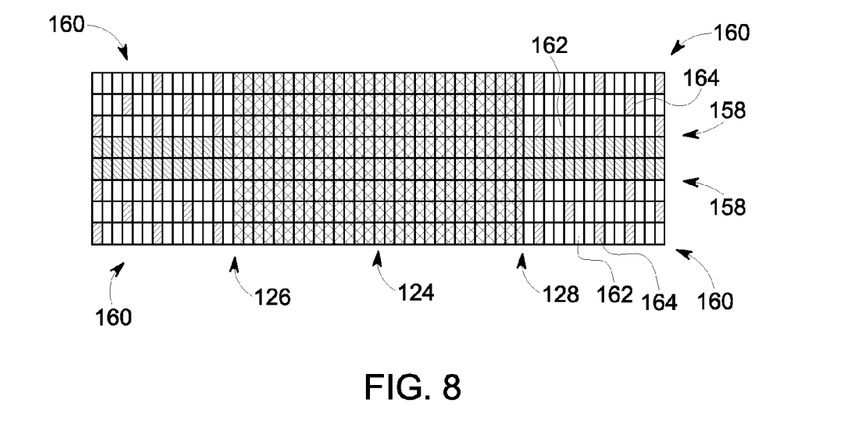
FIG. 8 illustrates another example of a depopulated x-ray detector according to an embodiment of the invention.

Further, it is to be understood that any pattern of empty and functioning blocks may be used to fill out four corner regions 160 of detector array 18. Thus, according to another embodiment illustrated in FIG. 8, four corner regions 160 are again delineated by z-boundaries 158 and by boundaries 126, 128. As can be seen, an alternate pattern of blocks 164 having functioning modules, and empty blocks 162, is illustrated therein. Further, the pattern of empty blocks 162 and blocks 164 with functioning modules needs not be symmetric or have a repeating pattern. Rather, blocks 164 with functioning modules may be randomly positioned within four corner regions 160.

Figure 9:
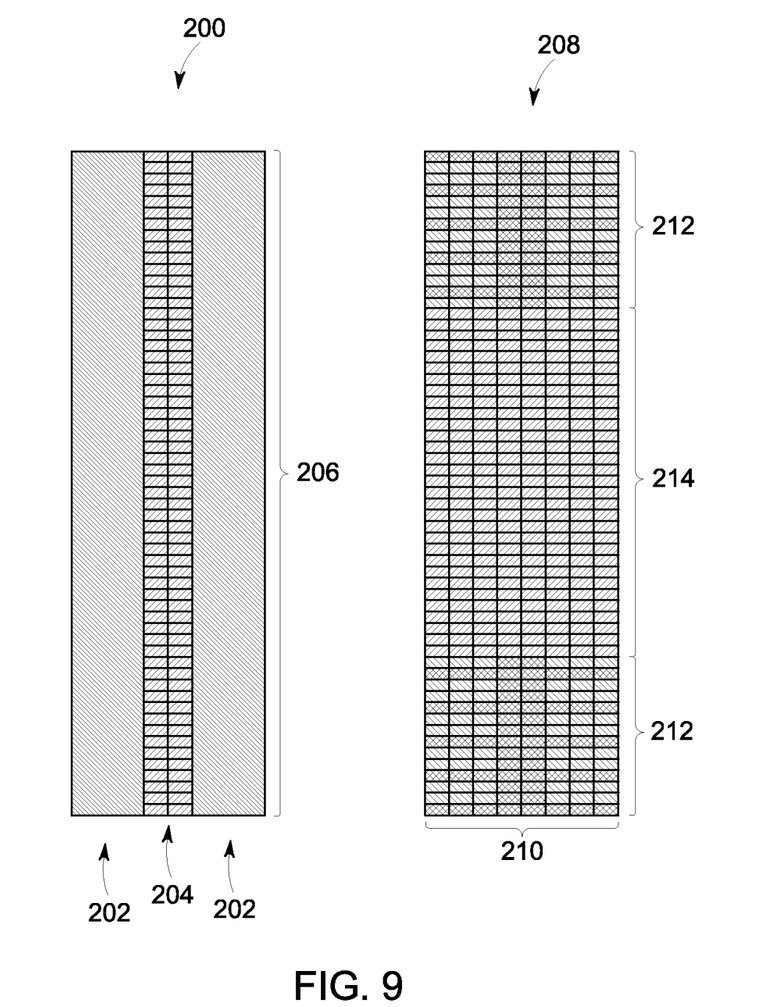
FIG. 9 illustrates a detector array for a full field-of-view (FOV) mode of operation and for a region-of-interest (ROI) mode of operation.
Figure 10:
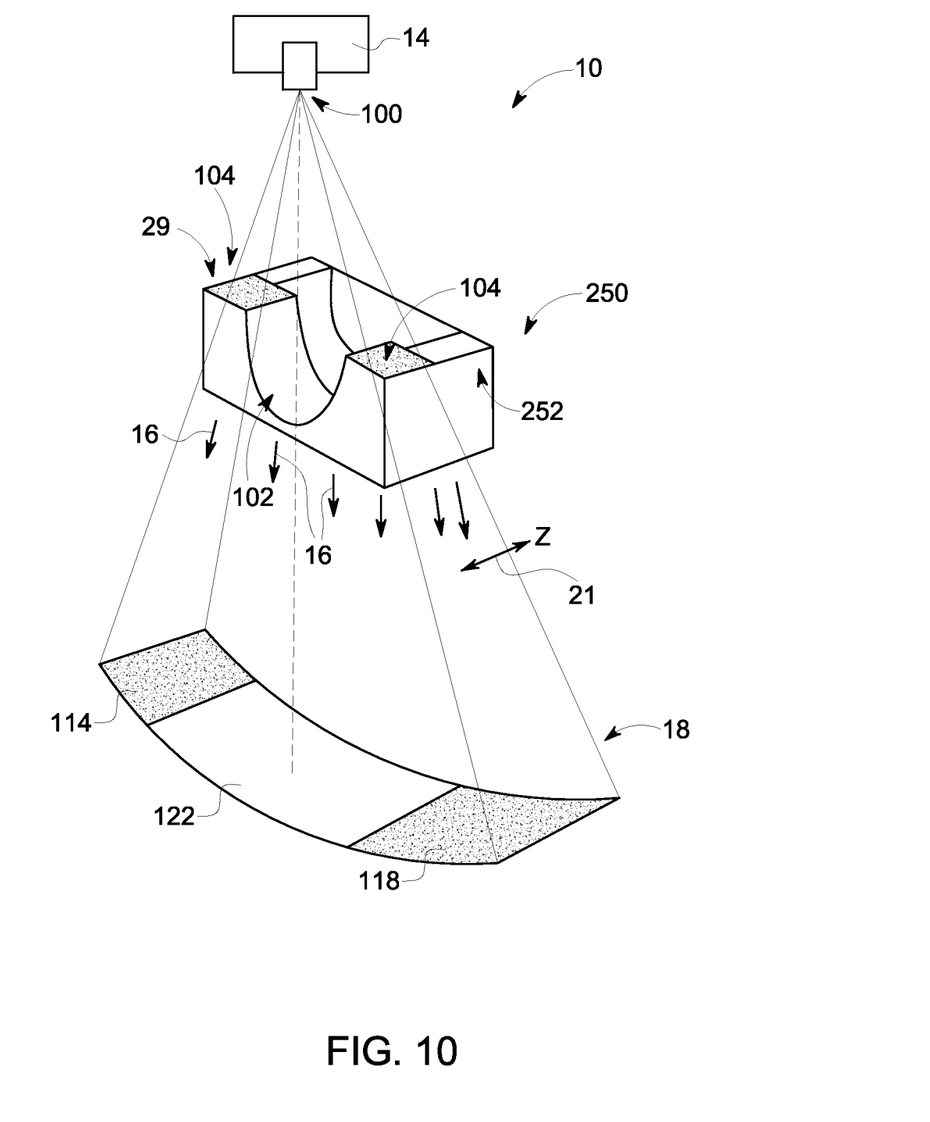
FIG. 10 illustrates an exemplary system arrangement having a bowtie filter and detector for accomplishing the two modes of operation of FIG. 9.

Thus, according to the invention and as illustrated in FIG. 9, a full FOV mode of operation 200 is illustrated in which outer slices 202 are blocked of x-rays using a pre-patient collimator (such as collimator 27 illustrated in FIGS. 1 and 2), and imaging data from central slices 204 is obtained over a full FOV 206 by using a large bowtie filter, as will be illustrated in FIG. 10. Also, the same detector arrangement can be used in an ROI mode of operation 208, in which all slices in a z-direction 210 are obtained by, for instance, opening collimator 27 to a much wider spacing than for full FOV mode of operation 200. However, in this mode, attenuated regions 212 are formed by using a small bowtie filter (relative in size to that used for full FOV mode of operation 200) and including attenuating materials 110 in region 104 as illustrated in FIG. 5, and data is obtained over a more limited ROI 214, which may correspond to ROI 62 as illustrated in FIG. 5.

Referring now to FIG. 10, a system illustrating a bowtie filter and a detector array for accomplishing the two modes of operation of FIG. 9 (full FOV and ROI) is illustrated. As described with respect to FIG. 5, system 10 includes x-ray source 14 having a focal spot 100, from which x-rays 16 emit toward detector array 18, which includes first detector sub-region 114, second detector sub-region 118, and central detector region 122. In this embodiment, a bowtie filter assembly 250 includes bowtie 29 as illustrated in FIG. 5. However, in this embodiment bowtie filter assembly 250 also includes a second bowtie filter 252 that is offset in z-direction 21, and includes a profile that may be used for a full FOV mode of operation. Thus, according to one embodiment and as described with respect to FIG. 9, imaging data may be obtained for ROI mode of operation 208 using bowtie filter 29 of bowtie filter assembly 250, and bowtie filter assembly 250 may be offset in z-direction 21 such that second bowtie filter 252 is positioned between focal spot 100 and detector assembly 18 in order to operate in full FOV mode of operation 200.

Figure 11:
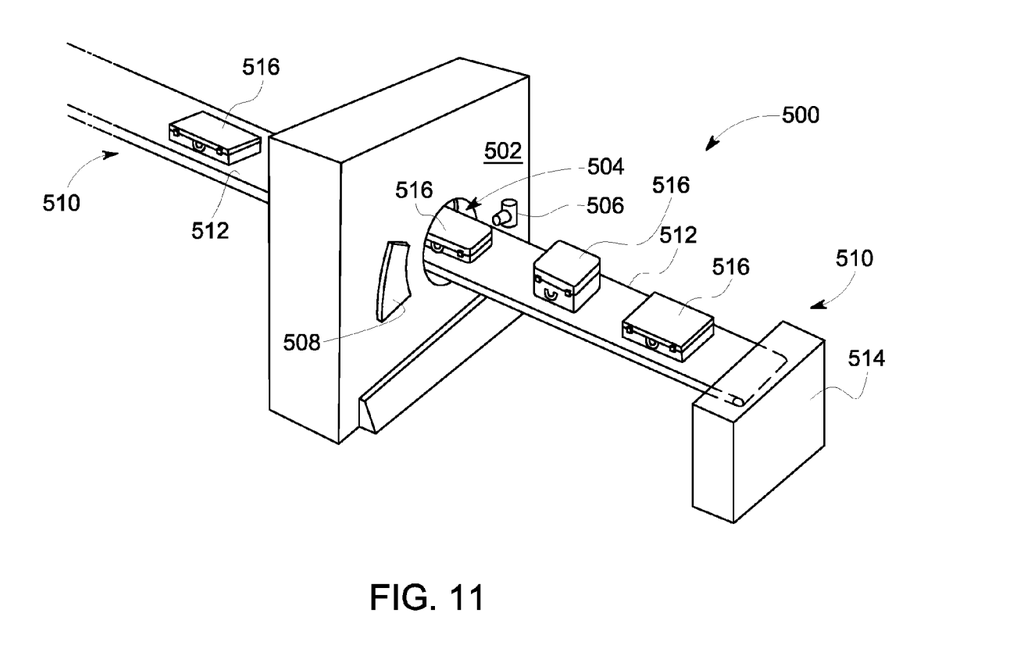
FIG. 11 is a pictorial view of a CT system for use with a non-invasive package inspection system.

Referring now to FIG. 11, package/baggage inspection system 500 includes a rotatable gantry 502 having an opening 504 therein through which packages or pieces of baggage may pass. The rotatable gantry 502 houses a high frequency electromagnetic energy source 506 as well as a detector assembly 508 having scintillator arrays comprised of scintillator cells similar to that shown in FIGS. 1 and 2. A conveyor system 510 is also provided and includes a conveyor belt 512 supported by structure 514 to automatically and continuously pass packages or baggage pieces 516 through opening 504 to be scanned. Objects 516 are fed through opening 504 by conveyor belt 512, imaging data is then acquired, and the conveyor belt 512 removes the packages 516 from opening 504 in a controlled and continuous manner. As a result, postal inspectors, baggage handlers, and other security personnel may non-invasively inspect the contents of packages 516 for explosives, knives, guns, contraband, etc.

A technical contribution for the disclosed method and apparatus is that it provides for a computer implemented method and apparatus of dose reduction in an imaging application.

One skilled in the art will appreciate that embodiments of the invention may be interfaced to and controlled by a computer readable storage medium having stored thereon a computer program. The computer readable storage medium includes a plurality of components such as one or more of electronic components, hardware components, and/or computer software components. These components may include one or more computer readable storage media that generally stores instructions such as software, firmware and/or assembly language for performing one or more portions of one or more implementations or embodiments of a sequence. These computer readable storage media are generally non-transitory and/or tangible. Examples of such a computer readable storage medium include a recordable data storage medium of a computer and/or storage device. The computer readable storage media may employ, for example, one or more of a magnetic, electrical, optical, biological, and/or atomic data storage medium. Further, such media may take the form of, for example, floppy disks, magnetic tapes, CD-ROMs, DVD-ROMs, hard disk drives, and/or electronic memory. Other forms of non-transitory and/or tangible computer readable storage media not list may be employed with embodiments of the invention.

A number of such components can be combined or divided in an implementation of a system. Further, such components may include a set and/or series of computer instructions written in or implemented with any of a number of programming languages, as will be appreciated by those skilled in the art. In addition, other forms of computer readable media such as a carrier wave may be employed to embody a computer data signal representing a sequence of instructions that when executed by one or more computers causes the one or more computers to perform one or more portions of one or more implementations or embodiments of a sequence.

According to an embodiment of the invention, a CT system includes a rotatable gantry having an opening to receive an object to be scanned, an x-ray source configured to project an x-ray beam toward the object, a detector array having a width in a slice-direction and configured to detect x-rays passing through the object, and a first bowtie filter positioned between the x-ray source and the opening. The first bowtie filter includes a first x-ray filtration region positioned to attenuate x-rays that pass through an isochannel of the detector array, a second x-ray filtration region positioned to attenuate x-rays that pass through channels of the detector array that are off-center in a channel direction from the isochannel, and an x-ray attenuation material positionable to attenuate the x-rays that pass through the channels of the detector array that are offcenter in the channel direction from the isochannel. The CT system also includes a data acquisition system (DAS) connected to the detector array and configured to receive outputs from the detector array, and a computer programmed to acquire projections of imaging data of the object from the DAS, and generate an image of the object using the imaging data.

According to another embodiment of the invention, a method of CT imaging includes projecting a beam of x-rays through a central portion of a bowtie filter and to a central portion of a detector array that includes an isochannel of the detector array, and projecting the beam of x-rays through a first non-central portion of the bowtie filter, the first non-central portion of the bowtie filter offset in a channel direction from the central portion of the bowtie filter, to a first non-central portion of the detector array, wherein the first non-central portion of the bowtie filter has a first x-ray attenuating material attached thereto.

According to another embodiment of the invention, a non-transitory computer readable storage medium having stored thereon a computer program comprising instruction which, when executed by a computer, cause the computer to obtain x-ray imaging data that is generated in a detector from x-rays that pass through a central region of a first portion of a bowtie filter that defines a first region-of-interest (ROI) and includes an isochannel of the detector, obtain x-ray imaging data that is generated in the detector from x-rays that pass through two regions of the first portion of the bowtie filter, wherein the two regions are offset in opposite channel directions from the isochannel, and wherein the x-ray imaging data from the two regions of the bowtie filter is generated from x-rays that pass through an x-ray attenuation material that is a material different from a material of the bowtie filter, and generate an image using the x-ray imaging data.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. A CT system comprising:
    a rotatable gantry having an opening to receive an object to be scanned;
    an x-ray source configured to project an x-ray beam toward the object;
    a detector array having a width in a slice-direction and configured to detect x-rays passing through the object;
    a first bowtie filter positioned between the x-ray source and the opening, the first bowtie filter comprising:
        a first x-ray filtration region positioned to attenuate x-rays that pass through an isochannel of the detector array;
        a second x-ray filtration region positioned to attenuate x-rays that pass through channels of the detector array that are offcenter in a channel direction from the isochannel; and
        an x-ray attenuation material positionable to attenuate the x-rays that pass through the channels of the detector array that are offcenter in the channel direction from the isochannel;
    a data acquisition system (DAS) connected to the detector array and configured to receive outputs from the detector array; and
    a computer programmed to:
        acquire projections of imaging data of the object from the DAS; and
        generate an image of the object using the imaging data.

2. The CT system of claim 1 wherein the x-ray attenuation material is attached to the second x-ray filtration region.

3. The CT system of claim 1 wherein the x-ray attenuation material is dynamically positionable, via a controller, in at least the channel direction.

4. The CT system of claim 1 wherein the x-ray attenuation material has an x-ray attenuation per unit thickness that is greater than an x-ray attenuation per unit thickness of the first bowtie filter.

5. The CT system of claim 1 wherein the first x-ray filtration region is further defined as a region passing x-rays therethrough to the detector array between:
    a first boundary of the detector array that is located in a first channel direction from the isochannel; and
    a second boundary of the detector array that is located in a second channel direction from the isochannel that is opposite the first channel direction.

6. The CT system of claim 5 wherein the first and second boundary regions correspond to a region-of-interest (ROI) of the object to be imaged.

7. The CT system of claim 6 wherein the computer is programmed to:
    low-pass filter measured signals outside the ROI that are obtained from x-rays passing through the x-ray attenuation material; and
    estimate missing signals that occur due to a lack of detector modules outside the ROI.

8. The CT system of claim 5 wherein the second x-ray filtration region is further defined as a region passing x-rays therethrough to the detector array that includes:

a first sub-region of the detector array extending from the first boundary in the first channel direction away from the isochannel; and a second sub-region of the detector array extending from the second boundary in the second channel direction away from the isochannel.

9. The CT system of claim 8 wherein the first and second sub-regions include a portion of the detector array that are offset in a slice direction to a third boundary from a center slice of the detector array.

10. The CT system of claim 9 wherein the first and second sub-regions are depopulated of detector modules over portions of the first and second sub-regions of the detector array.

11. The CT system of claim 1 comprising:
a pre-patient collimator positioned between the opening and the x-ray source and configured to collimate x-rays in a slice direction;
a second bowtie filter offset in a slice direction from the first bowtie filter; and
a controller configured to:
narrow an opening of the pre-patient collimator in the slice direction such that x-rays impinge the detector array at a first width that is narrower than the width of the detector array in the z-direction; and
re-position the x-ray attenuation material such that it does not attenuate x-rays that pass through the channel of the detector array that is offcenter in the channel direction from the isochannel.

12. The CT system of claim 11 wherein the controller is configured to translate the first and second bowtie filters in a slice direction such that the collimated x-rays pass through the second bowtie.

13. A method of CT imaging comprising:
projecting a beam of x-rays through a central portion of a bowtie filter and to a central portion of a detector array that includes an isochannel of the detector array; and
projecting the beam of x-rays through a first non-central portion of the bowtie filter, the first non-central portion of the bowtie filter offset in a channel direction from the central portion of the bowtie filter, to a first non-central portion of the detector array;
wherein the first non-central portion of the bowtie filter has a first x-ray attenuating material attached thereto.

14. The method of claim 13 wherein the central portion of the bowtie filter corresponds to a region-of-interest (ROI) of a patient to be imaged.

15. The method of claim 13 comprising:
applying a low-pass filter to measured signals that are received in the first non-central portion of the detector array; and
estimating a missed signal that occurs in the first non-central portion of the detector array.

16. The method of claim 13 wherein the first non-central portion of the detector array is depopulated of functioning detector cells over portions thereof.

17. The method of claim 13 comprising:
projecting the beam of x-rays through a second non-central portion of the bowtie filter, the second non-central portion of the bowtie filter offset in a channel direction that is opposite the channel direction to the first non-central portion of the bowtie filter, to a second non-central portion of the detector array;
wherein the second non-central portion of the bowtie filter has a second x-ray attenuating material attached thereto.

18. The method of claim 17 wherein at least one of the first and second attenuating materials has an attenuation per unit thickness that is greater than an attenuation per unit thickness of the bowtie filter.

19. A non-transitory computer readable storage medium having stored thereon a computer program comprising instruction which, when executed by a computer, cause the computer to:
obtain x-ray imaging data that is generated in a detector from x-rays that pass through a central region of a first portion of a bowtie filter that defines a first region-of-interest (ROI) and includes an isochannel of the detector;
obtain x-ray imaging data that is generated in the detector from x-rays that pass through two regions of the first portion of the bowtie filter, wherein the two regions are offset in opposite channel directions from the isochannel, and wherein the x-ray imaging data from the two regions of the bowtie filter is generated from x-rays that pass through an x-ray attenuation material that is a material different from a material of the bowtie filter; and
generate an image using the x-ray imaging data.

20. The non-transitory computer readable storage medium of claim 19 wherein the computer is further caused to dynamically re-position the x-ray attenuation material in conjunction with obtaining the x-ray imaging data.

21. The non-transitory computer readable storage medium of claim 19 wherein the computer is further caused to:
low-pass filter measured signals generated from the x-rays that pass through the x-ray attenuation material; and
estimate missing signals that occur due to a lack of detector modules outside the first ROI.

22. The non-transitory computer readable storage medium of claim 19 wherein the computer is further caused to:
narrow an opening of a pre-patient collimator in a slice direction such that x-rays impinge the detector at a first width that is narrower than a width of the detector in the z-direction; and
re-position the x-ray attenuation material such that it does not attenuate x-rays that pass through the two regions of the first portion of the bowtie filter that are offset in the opposite directions from the isochannel.

23. The non-transitory computer readable storage medium of claim 22 wherein the computer is further caused to:
translate the bowtie filter in a slice direction such that the collimated x-rays pass through a second portion of the bowtie filter, the second portion of the bowtie filter defining a second ROI that is different from the first ROI.

24. The non-transitory computer readable storage medium of claim 23 wherein the x-ray attenuation material is attached to the two regions of the bowtie filter.

* * * * *